United States Patent [19]

Goddard

[11] Patent Number: 5,059,188

[45] Date of Patent: Oct. 22, 1991

[54] EYE DROPPER ATTACHMENT

[76] Inventor: Larry C. Goddard, P.O. Box 849, Torrington, Wyo. 82240-0849

[21] Appl. No.: 500,558

[22] Filed: Mar. 28, 1990

[51] Int. Cl.$^5$ ............................................. A61M 35/00
[52] U.S. Cl. .................................... 604/300; 604/302
[58] Field of Search ................................ 604/295–302

[56] References Cited

U.S. PATENT DOCUMENTS

| | | |
|---|---|---|
| 2,676,592 | 4/1954 | Wood . |
| 2,722,216 | 11/1955 | Robbins . |
| 3,058,466 | 10/1962 | Routsong . |
| 3,872,866 | 3/1975 | Lelicoff . |
| 3,934,590 | 1/1976 | Campagna . |
| 4,002,168 | 1/1977 | Petterson . |
| 4,085,750 | 4/1978 | Bosshold . |
| 4,134,403 | 1/1979 | Johnsen . |
| 4,257,417 | 3/1981 | Gibilisco . |
| 4,468,103 | 8/1984 | Meckler ................................ 604/300 |
| 4,531,944 | 7/1985 | Bechtle . |
| 4,605,398 | 8/1986 | Herrick . |
| 4,685,906 | 8/1987 | Murphy . |
| 4,793,501 | 12/1988 | Beck ...................................... 215/235 |
| 4,917,253 | 4/1990 | Dutt ...................................... 215/235 |

*Primary Examiner*—Stephen C. Pellegrino
*Assistant Examiner*—Ralph A. Lewis
*Attorney, Agent, or Firm*—Shlesinger Arkwright & Garvey

[57] ABSTRACT

An attachment for connection to a dropper bottle containing eye drops for providing accurate positioning of the dropper opening of the eye drop bottle in relation to the nasal canthus as an aid to the insertion of eye drops into the eye. The eyedropper attachment includes an oval positioning ring to space the outlet opening a precise distance from the side of the user's nose and orbital rim. The attachment prevents contact of the nozzle of the bottle with the user's eye.

15 Claims, 2 Drawing Sheets

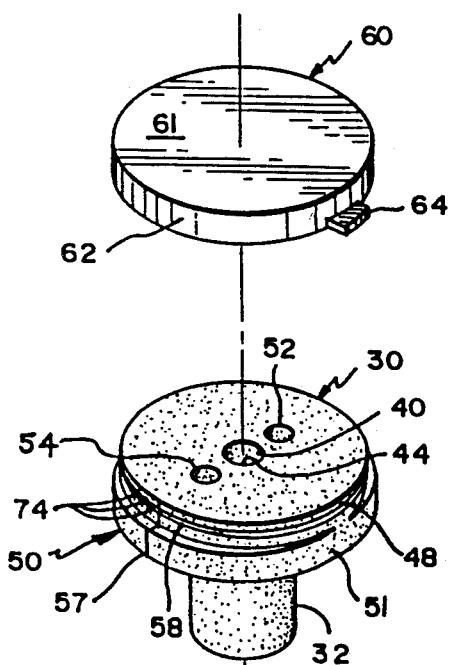
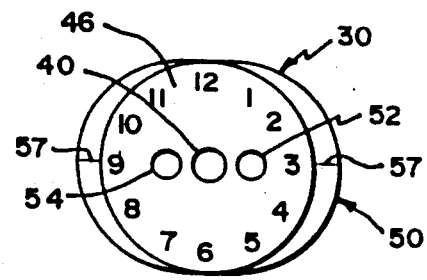
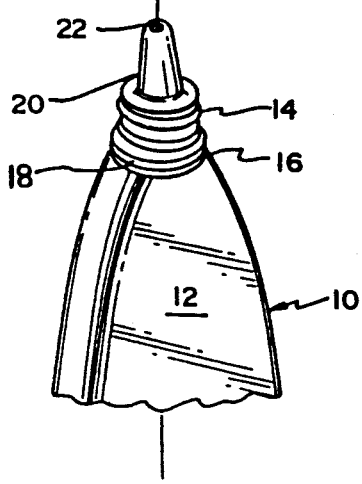
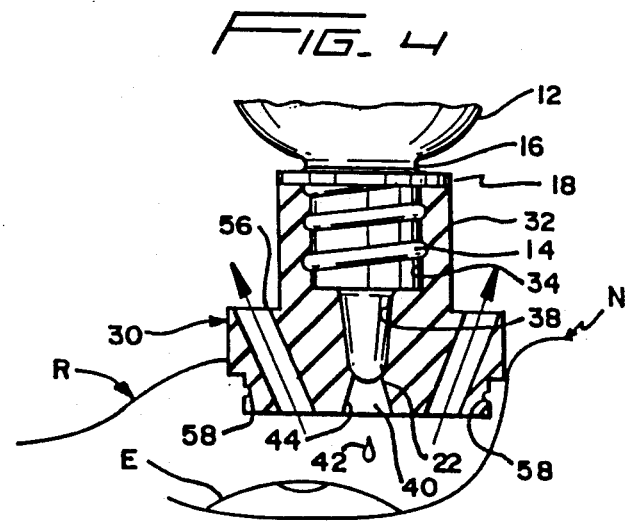
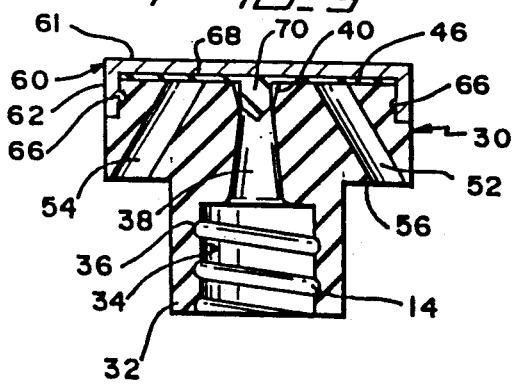
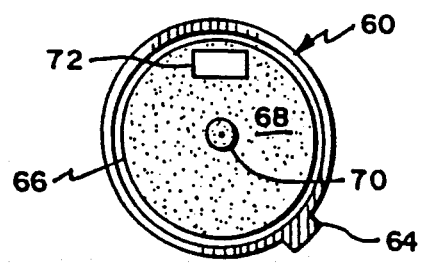

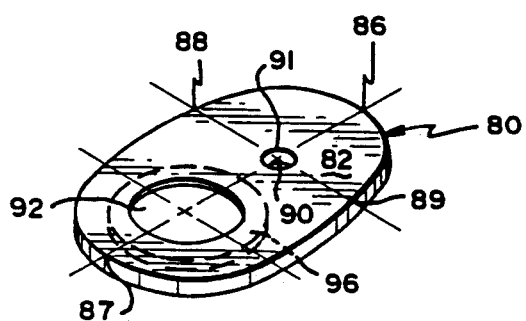
FIG_6
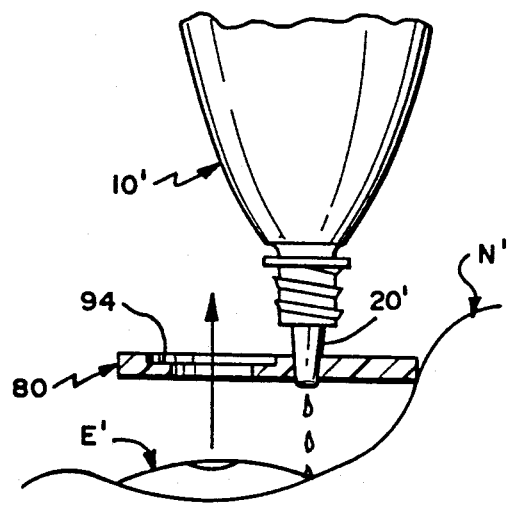
FIG_7
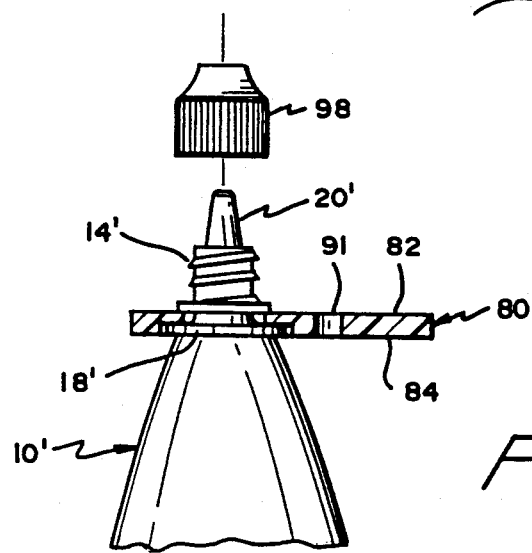
FIG_8
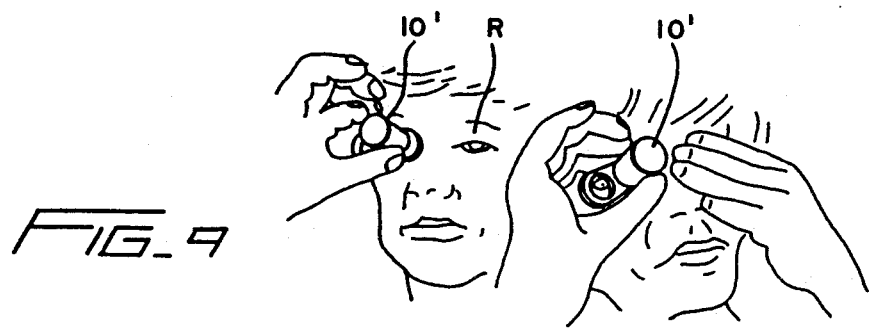
FIG_9

5,059,188

EYE DROPPER ATTACHMENT

FIELD OF THE INVENTION

This invention relates to an attachment for connection to a dropper bottle containing eye drops for providing accurate positioning of the dropper opening of the eye drop bottle in relation to the nasal canthus as an aid to the insertion of eye drops into the eye.

BACKGROUND OF THE INVENTION

The use of a squeezable eye drop bottle for the application of fluids to the eye has become a daily occurrence for millions of people. A wide variety of solutions, both prescription and non-prescription are available for application to the eyes. Contact lens wearers in particular apply wetting and lubricating solutions to their eyes periodically each day. The general procedures for applying such solutions to the eye includes tilting your head back while trying to position the dropper opening of the bottle directly over the eye. Only those with a steady hand and a high degree of coordination can regularly apply the eye drop solution to the eye without missing the eye altogether occasionally and wasting the solution. Improper application also leads to an inaccurate amount of solution being administered to the eye which causes many people to apply an extra drop or two to make sure that at least the required amount was administered. There is also the serious danger of accidental physical contact of the bottle nozzle with the eye which can produce serious eye injury.

In view of the above-noted problems, a variety of devices have been developed over the years to facilitate the selfadministration of drops. However, none of these devices have been satisfactory. Many are expensive and difficult to use, while others may be misplaced between uses because they do not remain with the dispenser bottle.

Prior art devices have not recognized that a natural potential pooling reservoir exists at the nasal portion of the lids toward the nose, anatomically referred to as the nasal canthus. A drop placed in this position will enter the space between the lids and therefore the eye. Even if the lids are closed, the drop quickly moves into the space as soon as the lids are opened.

After measuring the distance from the top of the orbital rim down, and the distance out from the bridge of the nose on many patients, the dimensions for a guide to position the eye drop bottle tip at the optimum spot have been determined. These results call for a slightly elliptical shaped guide which is 16 mm in the vertical direction down from the orbital rim and 18 mm in the horizontal direction from the bridge of the nose.

When the device is placed against the side of the nose with the dropper tip aimed toward the eye, the drop is dispensed exactly into the nasal canthus. None of the other devices previously referred to seem to specifically aim at a given spot for dispensing a drop.

In view of the above, it can be seen that there is a need for an eye drop administration device which provides accurate positioning of the eye dropper bottle relative to the eye for placement of the eye drops into the eye. The disclosed invention provides just such a device which eliminates the difficulties associated with administration of eye drops using an eye drop bottle alone.

OBJECTS AND SUMMARY OF THE INVENTION

Accordingly, the principle object of this invention is to provide a device which will position the outlet opening of an eye dropper in proper position for dispensing an eye drop into the nasal canthus.

Another object of the invention is to provide a sighting hole on either side of the central dispensing hole to permit the patient to sight or look through the device while dispensing the drop.

Yet another object of the invention is to provide a device which may be easily disinfected and cleaned.

Still another object of the invention is to provide a cap which fits over the device which will seal the dispensing opening.

Yet another object of the invention is to provide a means for securing the dispenser attachment to a bottle so that the device may be retained to the bottle both when in use and when not in use.

Still another object of the invention is to provide a device which will prevent eye injury from contact with the dropper nozzle.

In summary, therefore, this device is directed to an eye dropper bottle attachment for administering eye drops to the eye and which provides precise spacing of the eye dropper nozzle over the nasal canthus for the easy and safe administration of eye drops.

These and other advantages and objects of the invention will be readily apparent in view of the following description and drawings of the above-described invention. description and drawings of the above-described invention.

BRIEF DESCRIPTION OF THE DRAWINGS

The above and other features and advantages of the present invention will become apparent from the following detailed description of the preferred embodiment of the invention illustrated in the accompanying drawings, wherein:

FIG. 1 is an exploded perspective view of the dispenser attachment and cap for removable threadable attachment to a dispensing bottle;

FIG. 2 is a plan view of an eye drop dispensing attachment showing the oval positioning ring extending beyond the cap retaining portion;

FIG. 3 is a cross-sectional view of the cap and eye drop dispenser attachment;

FIG. 4 is a cross-sectional view of the eye drop dispensing attachment connected to an eye drop bottle in use placing a drop into the nasal canthus illustrating the lines of sight through the dispensing attachment;

FIG. 5 is an plan view of the cap bottom showing the stopper being centrally located thereon;

FIG. 6 is a perspective view of another embodiment of the invention showing a sighting hole and a dispenser nozzle attachment hole spaced therefrom;

FIG. 7 is an elevational view of the eye drop dispenser attachment of FIG. 6 in cross-section in an in-use position with the bottle nozzle extending into the eye drop dispensing hole and the sight hole spaced therefrom;

FIG. 8 is an elevational view of the dispenser attachment in cross-section in its storage position connected to an eye drop dispenser bottle; and, FIG. 9 illustrates how the invention is used to insert fluid into the eye using the embodiment of FIGS. 6–8.

DETAILED DESCRIPTION OF THE INVENTION

In FIG. 1, a dispensing bottle 10 of conventional design is shown and is generally formed of plastic and has a relatively flexible fluid-holding chamber 12. The dispensing bottle 10 includes a male-threaded cap retaining portion 14 integrally connected to the bottle neck 16 which is most clearly shown in FIGS. 3 and 4. Encircling the bottle neck 16 is a cap seat flange 18.

A dispensing nozzle dropper 20 extends from the threaded cap retaining portion 14. Nozzle 20 includes a dispensing opening 22 which allows the passage of fluid from the fluid-holding chamber 12 through the opening 22.

A dispensing bottle 10 may contain from about 5 ml to up to several ounces of ophthalmic fluid. The size of the threaded cap retaining portion 14 on a dispensing bottle 10 will usually range between 10 mm on a 5 ml bottle up to about 15 mm on a several ounce bottle 10. The length of the eye dropper nozzle 20 is generally about 12 mm in length regardless of the size of the dispensing bottle 10. The nozzle hole opening 22 is about 1 mm to 2 mm in diameter.

The eye dropper attachment 30 as shown in FIGS. 1-4, is formed of flexible, resilient plastic material. Eye dropper attachment 30 includes a dispensing bottle attachment portion 32 having an enlarged axial bore 34 therein with female threads 36 for complimentary engagement with the male-threaded portion 14 of dispensing bottle 10. The resilient properties of the eye dropper attachment 30 allows the dispensing bottle attachment portion 32 to expand from an initial axial bore 34 diameter of about 10 mm to a diameter large enough to connect eye dropper attachment 30 to a dispensing bottle 10 having a threaded cap retaining portion 14 of a diameter of 15 mm.

A conical passage 38 extends from axial bore 34 and is of a complementary configuration to that of the exterior surface of eye dropper nozzle 20. Conical passage 38 is of about the same length as eye dropper nozzle 20 and preferably forms a fluid-tight seal around nozzle 20. The narrowest circumference of conical passage 38 is at nozzle opening 22, as shown in FIG. 4 and is about 3 mm in diameter.

A conical-shaped passageway or outlet 40 extends from conical passage 38 which allows a drop of fluid 42, as shown in FIG. 4, to pass from nozzle opening 22 through outlet 40 when bottle 10 is inverted in a dispensing position. Outlet 40 has a frusto-conical surface 44, which flares outwardly from the narrow portion of conical passage 38 to a diameter of about 4 mm at the top flat surface 46.

As best shown in FIG. 4, the nozzle 20 does not extend through outlet 40, but is recessed from top flat surface 46, thereby preventing inadvertent contact with the user's eye E.

Top flat surface 46 is circular and preferably has a diameter of about 32 mm which provides a radius to the center of outlet 40 of about 16 mm. A sidewall 48 extends perpendicularly from the perimeter of top flat surface 46, a distance of about 4 mm. Joined at the bottom of the sidewall is an oval-shaped positioning ring 50. The smallest radius of the oval positioning ring 50 is about 16 mm where its sidewall 52 becomes flush with the sidewall 48 of top surface 46. The largest radius of oval positioning ring 50 is about 18 mm.

The positioning ring 50 provides the important function of spacing outlet opening 40 the proper distance from a user's nose N and orbital rim R so a drop 42, can enter the eye E. The user can apply the drop 42 a distance of 16 mm down from the orbital rim R and 18 mm from the side of the user's nose N using the dropper attachment 30.

Preferably, a pair of sighting holes 52 and 54, having diameters of about 4 mm, extend from top surface 46 and exit at bottom surface 56 of positioning ring 50. Positioning marks 57 help to align the positioning ring 50 with respect to the nose N. Sighting holes 52 and 54, are angled at about 45 degrees to permit the patient to sight or look through the dropper attachment 30 while dispensing a drop 42, thus distracting the eye's attention to reduce blinking as a reflex action when the drop 42 is falling into the eye. Sighting holes 52 and 54 are aligned with outlet opening 40 and each of holes 52 and 54 are spaced about 2.5 mm from outlet opening 40. A female cap connecting ring 58 is located on sidewall 48 to facilitate secure engagement with cap 60. Ring 58 forms a groove and helps to lock cap 60 onto the dropper attachment 30.

A cap 60 is shown in FIGS. 1, 3 and 5. Cap 60 is preferably circular and corresponding in diameter to the diameter of top flat surface 46. Cap 60 has a round top flat surface 61 and a depending side wall 62 sized for complementary engagement with sidewall 48, and a lifting tab 64 to aid in removal of the cap from sidewall 48.

As shown in FIG. 3, cap 60 covers top flat surface 46 and sidewall 48 when it is engaged with dropper attachment 30. Cap 60 rests upon positioning ring 50 where positioning ring 50 extends beyond sidewall 48. Cap 60 overhangs positioning ring 50 where positioning ring 50 is flush with sidewall 48. Cap 60 includes a frictional engagement ridge 66 on the interior surface of depending sidewall 62 for engaging sidewall 48. Cap 60 is preferably formed of relatively rigid plastic material which is less flexible than the dropper attachment 30. Cap 60 includes a liner 68 on the interior thereof which is formed of a plastic material of similar composition to that of eye dropper attachment 30.

Integrally attached to liner 68 is a stopper 70 which extends about 4 mm from liner 68 Stopper 70 is about 3.5 mm in diameter to plug outlet 40 and prevent fluid from escaping from dispenser bottle 10 when eye dropper attachment 30 is connected to cap 60. Attachment of cap 60 to the eye dropper attachment 30 allows eye dropper attachment 30 to remain connected to the dispenser bottle 10 between administrations of fluid to the eye E.

Stopper 70 is preferably formed of thin plastic material such as urethane and is hollow and therefore collapsible to accommodate and seal any bottle nozzle opening 22.

Cap 60 also includes a window 72 therein for viewing a number 1-12 on the top surface 46 of dispenser attachment 30. Each number 1-12 corresponds to an hour of the day for the next application or to the number of drops taken. Cap 60 is rotated to align the window 72 with one of the corresponding numbers 1-12 which are spaced about the top flat surface 46 near the depending sidewall 48 as shown in FIG. 2.

A series of indentations 74 may be located around the sidewall 48 to provide an obvious stopping point at each number as the cap 60 is rotated.

Another embodiment of the invention is shown in FIGS. 6, 7, 8 and 9. In this embodiment, like parts to those of the other embodiment previously described will be referred to with like prime numbers.

In FIG. 6 an eye drop administration aid 80 is shown having an oval exterior shape. Top surface 82 and bottom surface 84 are flat. The length of administration aid 80 is about 50 mm in its longest dimension measured between end 86 and end 87, and is about 32 mm in width measured along a line perpendicular to the longest dimension extending between sides 88 and 89 through the center 90 of connecting opening 91. The distance from the center 90 to the edge 86 is about 18 mm. Administrative aid 80 has a thickness of about 4 mm.

The connecting opening 91, having a diameter of about 4 mm, is spaced from edge 86 a distance of about 16 mm. As best shown in FIG. 7 the nozzle 20' is engageable with opening 91 to secure administration aid 80 to eye dropper bottle 10'.

Opening 92 acts as a sighting hole when administration aid 80 is in use as shown in FIG. 9. Opening 92 is preferably of a diameter of about 16 mm. When administration aid 80 is not in use, it can be stored on a dispensing bottle 10' as shown in FIG. 8. When administrative aid 80 is stored on dispensing bottle 10', nozzle 20' is inserted through opening 92 as well as male-threaded portion 14' until recessed area 94 encircling opening 92 engages the cap seat flange 18'. Recessed area 94 forms about a 2 mm ring about opening 92 and is preferably large enough to slide over cap seat flange 18' so that ledge 96 rests on flange 18'. Original bottle cap 98, is then secured on the bottle 10' to seal bottle 10' and to securely hold administrative aid 80 in place.

To use administration aid 80, end 86 is placed against the side of the bridge of the nose N to space the center 90 of connecting opening 91 a distance of about 18 mm from nose N and one of sides 88 or 89 engages the orbital rim R to space the center 90 a distance of about 16 mm from orbital rim R. The patient looks through the large hole 92, and gently squeezes dispensing bottle 10' to dispense the drop 42'.

Both eye dropper attachment 30 and administration aid 80, are washable and constructed of materials which are dishwasher safe such as polyethylene.

While this invention has been described as having preferred designs, it is to be understood that it is capable of further modification, uses and/or adaption of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. A dispensing attachment for use with a fluid-holding container including a dropper having a dispensing opening for eye drops, comprising:
   (a) a container positioning means for correct positioning of said container relative to a user's eye and nose prior to dispensing a drop therein;
   (b) said container positioning means including means for receiving said dropper;
   (c) said means for receiving said dropper including a through passageway for permitting dispensed drops to fall into the user's eye;
   (d) said container positioning means including means for accurately positioning said passageway over a user's nasal canthus, including means for contacting a side of a user's nose and orbital rim;
   (e) said means for contacting a side of a user's nose and orbital rim extending radially from said passageway forming an oval ring;
   (f) said container positioning means having a sighting means forming a hole therein; and
   (g) said container positioning means having a planar surface, and said sighting means forming a hole for sighting through located in said planar surface and said passageway forming a hold for eye drops to pass through located in said planar surface.

2. The dispensing attachment, as defined in claim 1, wherein:
   (a) said sighting means forms a hollow passage extending angularly relative to said means for receiving said container dropper.

3. The dispensing attachment as defined in claim 2,
   (a) said sighting means extends at an angle of about 45 degrees relative to said means for receiving said container dropper.

4. The dispensing attachment of claim 1, wherein:
   (a) said container positioning means includes an oval positioning ring for accurately positioning said passageway over a user's nasal canthus.

5. The dispensing attachment as defined in claim 1,
   (a) the distance from the center of said outlet opening to a side of said container positioning means ranges from about 16 mm to about 18 mm.

6. The dispensing attachment of claim 1, wherein:
   (a) said container positioning means includes a circular cap retaining means thereon.

7. The dispensing attachment as defined in claim 6, further comprising:
   (a) cap means for covering said passageway.

8. The dispensing attachment as defined in claim 7,
   (a) said cap means includes ridge means for frictionally engaging a side surface of said circular cap retaining means.

9. The dispenser attachment of claim 7, wherein:
   (a) said cap means includes stopper means for sealingly engaging said passageway to prevent the passage of fluid therethrough.

10. A cap for sealingly engaging an eye dropper bottle attachment means having a cap-engaging surface and a central passageway for allowing fluid from the bottle to pass through the eye dropper bottle attachment means, said cap comprising:
    (a) covering means having a flat surface having a depending side wall extending therefrom;
    (b) said side wall including frictional engagement means for releasably securing said cap to the eye dropper bottle attachment;
    (c) said flat surface including stopper means extending therefrom in the same direction as said depending side wall for engaging the central passageway and preventing the passage of fluid therethrough, and
    (d) said flat surface includes a window means formed therein for viewing indicia on the eye dropper bottle attachment means.

11. The cap as defined in claim 10, wherein:
    (a) said covering means includes a liner on an interior surface thereof; and
    (b) said stopper means is integrally joined with said liner.

12. The cap is defined in claim 10, wherein:

(a) said covering means includes a lifting means thereon extending outwardly from said side wall for facilitating separation of said covering means from the eye dropper bottle attachment means.

13. The cap as defined in claim 11, wherein
    (a) said stopper means is centrally positioned relative to said side wall and extends a distance of about 4 mm therefrom for plugging the central passageway of the eye dropper bottle attachment means and preventing the escape of fluid therethrough.

14. An eyedropper bottle attachment for connection to an eye drop dispensing bottle having a dispensing opening for eye drops, the attachment comprising:
    (a) a container positioning means for correct positioning of said container relative to a user's eye and nose prior to dispensing a drop therein;
    (b) said container positioning means including means for receiving the dropper;
    (c) said connecting means for receiving the dropper having extending therethrough a passageway so that drops from the eye drop dispensing bottle may pass through said means for receiving the dropper and exit through said passageway;
    (d) said container positioning means including means for accurately positioning said passageway over a user's nasal canthus including means for contacting a side of a user's nose and orbital rim;
    (e) said means for contacting a side of a user's nose extending radially from said passageway forming an oval ring;
    (f) said container positioning means having sighting means forming a hole therein;
    (g) said container positioning means having a planar surface, and said sighting means forming a hole for sighting through located in said planar surface and said passageway being located in said planar surface; and,
    (h) a removably attachable cap means for engaging said container positioning means and preventing the escape of fluid through said passageway.

15. The eyedropper bottle attachment of claim 14, wherein:
    (a) said removably attachable cap means includes a top surface having window means therein for viewing indicia on said planar surface.

* * * * *